US007148199B2

(12) United States Patent
Neu et al.

(10) Patent No.: US 7,148,199 B2
(45) Date of Patent: Dec. 12, 2006

(54) ARGINYL-GLUTAMINE DIPEPTIDE FOR TREATMENT OF PATHOLOGICAL VASCULAR PROLIFERATION

(75) Inventors: Josef Neu, Gainesville, FL (US); Maria B. Grant, Fairfield, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/951,150

(22) Filed: Sep. 27, 2004

(65) Prior Publication Data
US 2005/0070484 A1  Mar. 31, 2005

Related U.S. Application Data

(60) Provisional application No. 60/506,413, filed on Sep. 26, 2003.

(51) Int. Cl.
    *A61K 38/05* (2006.01)
(52) U.S. Cl. .................................................. 514/19
(58) Field of Classification Search .................. None
    See application file for complete search history.

(56) References Cited

U.S. PATENT DOCUMENTS

| | | | |
|---|---|---|---|
| 4,055,669 A | | 10/1977 | Kelly et al. |
| 4,303,692 A | * | 12/1981 | Gaull .......................... 426/580 |
| 4,340,592 A | | 7/1982 | Adibi |
| 4,673,578 A | | 6/1987 | Becker et al. |
| 4,871,557 A | | 10/1989 | Linscott |
| 5,189,016 A | | 2/1993 | Madsen et al. |
| 5,561,111 A | | 10/1996 | Guerrant et al. |
| 5,576,351 A | | 11/1996 | Yoshimura et al. |
| 5,759,547 A | | 6/1998 | Maione |
| 6,051,270 A | | 4/2000 | Monte |
| 6,511,696 B1 | * | 1/2003 | Gohman et al. ............. 426/601 |
| 2002/0132779 A1 | | 9/2002 | Green et al. |
| 2002/0183263 A1 | * | 12/2002 | Hageman et al. ............. 514/23 |
| 2003/0027769 A1 | | 2/2003 | Scialdone et al. |
| 2003/0109458 A1 | | 6/2003 | Haviv et al. |
| 2004/0138133 A1 | | 7/2004 | Cheresh et al. |
| 2005/0070484 A1 | * | 3/2005 | Neu et al. ...................... 514/19 |

FOREIGN PATENT DOCUMENTS

| | | | |
|---|---|---|---|
| EP | | 0 182 356 | 9/1985 |
| JP | | 02119762 A | * 5/1990 |
| WO | | WO 98/09985 | 3/1998 |
| WO | | WO 00/33662 | 6/2000 |
| WO | | WO 01/98362 | 12/2001 |
| WO | | WO 02/062371 | 8/2002 |
| WO | | WO 03/017787 | 3/2003 |
| WO | | WO 03/082918 | 10/2003 |

OTHER PUBLICATIONS

"Diabetic Retinopathy" http://medicalcenter.osu.edu/patientcare/healthinformation/diseasesandconditions/eyecare/disorders/diabetic, accessed Aug. 18, 2005. 3 pages.*
"Retinopathy of Prematurity" Kellog Eye Center U of Michigan http://www.kellogg.umich.edu/patientcare/conditions/retinopathy.prematurity.html, accessed Aug. 18, 2005. 2 pages.*
"Diabetic Retinopathy. What you should know". NIH Publication 03-2171. US Dept HHS, NIH, NEI. Revised Sep. 2003. 18 pages.*
"Retinopathy of Prematurity" (Section 19, chapter 260)in The Merck Manual of Diagnosis and Therapy, 17th ed. (web version) M.H. Beers and R.A. Berkow, eds. Accessed Aug. 18, 2005 http://www.merck.com/mrkshared/mmanual/section19/chaper260/2601.jsp.*
"Retinopathy of Prematurity" The Lucile Packard Children's Hospital, web document, accessed Aug. 18, 2005 http://www.lpch.org/DiseaseHealthInfo/HealthLibrary/hrnewborn.rpm.html.*
English Translation for JP-02-119762, Koji et al.*
Abcouwer S. et al., Response of VEGF expression to amino acid deprivation and inducers of endoplasmic reticulum street, *Invest Ophthalmol Vis Sci*, Aug. 2002, p. 2791-8, vol. 43, No. 8.
Adibi, S. et al., "Influence of Molecular Structure on Half-life and Hydrolysis of Dipeptides in Plasma: Importance of Glycine as N-Terminal Amino Acid Residue," *Metabolism* (1986), 35(9):830-836.
Cynober, L., "Place des Nouveaux Substras Azotes en Nutrition Artificielle Perioperatoire de l'Adulte," *Ann. Fr. Anesth. Reanim.* (1995), 14(Suppl. 2):102-105. (Abstract in English).
Database WPI. Derwent Publications Ltd., London GB; AN 1997-037972; XP0021XP002195568 & JP 08 295633 A (Otsuka Seiyaku Kogyo KK) Nov. 12, 1996, Abstract.
Le Boucher, J. et al., "Modulation of immune Response With Ornithine A-Ketoglutarate in Burn Injury: An Argine or Glutamine Dependency?" *Nutrition* (1999), 15(10):773-777.
Matilla B. et al., "Effects of Parenteral Nutrition Supplemented with Glutamine or Glutamine Dipeptides on Liver Antioxidant and Detoxication Systems in Rats," *Nutrition, Nutrition* (2000), 16:125-128.

(Continued)

Primary Examiner—Cecilia J. Tsang
Assistant Examiner—Andrew D. Kosar
(74) Attorney, Agent, or Firm—Saliwanchik, Lloyd & Saliwanchik

(57) ABSTRACT

The subject invention provides dipeptides useful in preventing pathological proliferation of blood vessels. The dipeptides of the subject invention are particularly advantageous because they are stable, bioavailable, and can be formulated in an aqueous solution.

3 Claims, 2 Drawing Sheets

OTHER PUBLICATIONS

Mattox, T. W. et al., "Recent Advances: Parenteral Nutrition Support," *Nutrition* (1995), 29(2):174-180.

Miyazawa, K. et al., "Amino-Acids and Peptide in 7 Species of Marine Green Algae," *Journal of the Faculty of Fisheries and Animal Husbandry Hiroshima* (1976), 15:161-169. (Abstract from Database Biosis 'Online').

Moinard, C. et al., "Involvement of Glutamine, Arginine, and Polyamines in the Action of Ornithine α-Ketoglutarate on Macrophage Functions in Stressed Rats," *Journal of Leukocyte Biology* (2000), 67:834-840.

Neu, J. et al., "Glutamine Nutrition and Metabolism: Where Do We Go From Here?" *The FASEB Journal* (1996), 10:829-837.

Robinson, L. E. et al., "Amino Acid Nutrition and Immune Function in Tumour-Bearing Rats: A Comparison of Glutamine-, Argine- and Ornithine 2-Oxoglutarate-Supplemented Diets," *Clinical Science* (1999), 97:658-669.

Weckbecker, G. et al., "The Somatostatin Analog Octreotide as Potential Treatment for Re-Stenosis and Chronic Rejection," *Transplantation Proceedings* (1997), 29:2599-2600.

* cited by examiner

ARGINYL-GLUTAMINE DIPEPTIDE FOR TREATMENT OF PATHOLOGICAL VASCULAR PROLIFERATION

CROSS-REFERENCE TO RELATED APPLICATIONS

This application claims the benefit of U.S. provisional application Ser. No. 60/506,413, filed Sep. 26, 2003.

BACKGROUND OF THE INVENTION

People suffering from visual impairment face many challenges in performing routine daily activities and/or may not be able to fully enjoy the visual aspects of their surroundings. Of particular concern with regard to the current invention are visual impairments caused by damage to the retina, which occur in conditions such as diabetic retinopathy and retinopathy of prematurity.

Diabetic retinopathy is a progressive disease characterized by abnormalities of the blood vessels of the retina caused by diabetes, such as weakening of the blood vessel walls, leakage from the blood vessels, and bleeding and scarring around new vessels. Diabetic retinopathy results in impairment of a person's vision causing severely blurred vision and, potentially, blindness.

Diabetes affects over 16 million Americans. The World Health Organization indicates that diabetes afflicts 120 million people worldwide, and estimates that this number will increase to 300 million by the year 2025. Diabetics are faced with numerous complications including kidney failure, non-traumatic amputations, an increase in the incidence of heart attack or stroke, nerve damage, and loss of vision. Diabetic retinopathy is a form of visual impairment often suffered by diabetics.

Due to significant medical advancements, diabetics are able to live much longer than in the past. However, the longer a person has diabetes the greater the chances of developing diabetic retinopathy. Affecting over 5.3 million Americans, diabetic retinopathy is the leading cause of blindness among adults in the United States. Annually, in the United States, between 12,000 and 24,000 people lose their sight because of diabetes.

While management of diabetic retinopathy has improved, risk of complications, such as loss of visual acuity, loss of night vision and loss of peripheral vision, remains significant and treatment sometimes fails. Currently, laser photocoagulation is the most effective form of therapy for advanced disease. Unfortunately, current treatment options are inadequate and the disease is often progressive even with successful glucose control.

Retinopathy of prematurity (ROP) is a disorder of retinal blood vessel development in the premature infant. Under normal development, blood vessels grow from the back central part of the eye out toward the edges. In premature babies, this process is not complete and the abnormal growth of the vessels proliferate leading to scar tissue development, retinal detachment and possibly complete blindness.

ROP is the major cause of blindness in children under the age of 7. The salient pathological features are neovascularization in the retinal vascular endothelium with edema and breakdown in the blood-retinal barrier (BRB) that leads to hemorrhage, tissue damage and retinal scarring ultimately leads, in the severest cases, to blindness.

Improved care in the neonatal intensive care unit has reduced the incidence of retinopathy of prematurity in moderately premature infants. Ironically, however, increasing rates of survival of very premature infants, who would have had little chance of survival in the past, has increased the occurrence of retinopathy of prematurity. Since these very premature infants are at the highest risk of developing ROP, it is of great concern that the condition may actually be becoming more prevalent again.

For those babies in whom retinopathy progresses, treatment is necessary. Cryotherapy and laser treatment have some effect in advanced stages of the disease, saving a degree of vision in a proportion of the eyes that would otherwise have been blinded, but prevention awaits a better understanding of major causative factors and underlying pathophysiology.

Current research shows promise that the prevention of retinal blood vessel damage, which marks retinopathy, may be achieved by the utilization of certain compounds. It has been demonstrated that, in retinal epithelial cells, glutamine deprivation can lead to upregulation of vascular endothelial growth factor (VEGF) expression (Abcouwer S. et al., "Response of VEGF expression to amino acid deprivation and inducers of endoplasmic reticulum stress," Invest Ophthalmol Vis Sci, August 2002, pp. 2791–8, Vol. 43, No. 8). Most sick premature infants are deprived of glutamine during the time they receive supplemental oxygen, a known predisposing factor in the development of ROP. The over expression of VEGF during this time period is also thought to be involved in the pathogenesis of ROP. Providing glutamine supplements during this time period could potentially down-regulate VEGF. Arginine is a substrate for the reaction that produces nitric oxide, a very potent vasodilator; vasodilation in retinal blood vessels also prevents neovascularization. Nitric oxide also has numerous other beneficial effects and is now commonly used for treatment of lung disease in critically ill infants.

It is well known that proteins are converted to amino acids in the digestive system and that the resulting amino acids are used by the body for growth and development. Proteins and peptides administered for therapeutic or preventative measures are also well-known. Oligopeptides are better absorbed in the intestines than individual amino acids.

European Patent Application No. 0,182,356 discloses a nutritional composition containing at least one oligopeptide consisting of a dipeptide or a tripeptide wherein the N-terminal amino acid residue is selected from the class consisting of alanine, lysine and arginine.

One group conducting research in this area concluded that glycine is generally superior to other amino acids as the N-terminal amino acid residue in a dipeptide. This superiority was attributed to a greater fraction of such an intravenously administered dipeptide reaching the tissues. S. Adibi et al., Influence of Molecular Structure on Half-life and Hydrolysis of Dipeptides in Plasma: Importance of Glycine as N-Terminal Amino Acid Residue, 35 Metabolism 850, 835 (1986).

Two European patents, 0,087,751 and 0,087,750 disclose water-soluble peptides. The '751 patent discloses a method to parenterally administer low water-soluble amino acids. Two amino acids, tyrosine and cystine, individually have low solubility in water. These amino acids, however, are clinically useful and, therefore, it was desirable to find an effective formulation. The '751 patent describes an infusion method which involves bonding these relatively insoluble amino acids to the amino acid lysine to produce a tripeptide.

The '750 patent discloses the infusion of glutamine as a derivative substituted by α-aminoacyl residues on the α amino group. That is, glutamine is in the "c-terminal" position, in that its alpha amino nitrogen becomes part of the peptide bond with the other amino acid. The preferred dipeptide preparation disclosed in the '750 patent is alanyl-glutamine. The aminoacylation of glutamine is reported to achieve a stabilization of the terminal amide group.

Experiments involving the use of total parenteral nutrition (TPN) containing glycyl-glutamine dipeptides, however, suggest potential adverse effects of the TPN formulation containing glycyl-glutamine (U.S. Pat. No. 5,189,016).

Also, the use of an arginyl-glutamine dipeptide for the prevention of muscle breakdown and microbial infections has recently been described. See, WO 03/017787. These amino acids have also been described in complex compositions (Miyazawa et al. (1976) *Journal of Faculty of Fisheries and Animal Husbandry Hiroshima* 15(2):161–169; and JP 2119762).

Two commercially available dipeptides of glutamine are DIPEPTIVEN™, which is an alanyl-glutamine (Fresenius Laboratories, Germany) and GLAMIN™(Pharmacia and Upjohn Laboratory, Sweden), which is an amino acid solution containing glycyl-glutamine dipeptide. To this date, there are no published studies of the arginyl-L-glutamine dipeptide.

With the increase of adult onset diabetes, longer life span for diabetics and high rate of survival of very premature infants, many individuals are now at even greater risk for developing retinopathy. Although treatment options, such as laser therapy, exist for both conditions, the results are inadequate and the disease often remains progressive. There remains a great need in the art for compositions which prevent retinal diseases.

BRIEF SUMMARY OF THE INVENTION

The subject invention provides materials and methods useful in preventing proliferation of abnormal blood vessels. The prevention of the over-proliferation of these blood vessels according to the subject invention is particularly advantageous for treatment of certain ocular conditions including premature infants at risk for retinopathy of prematurity and individuals at risk for diabetic retinopathy.

In a preferred embodiment of the subject invention, the amino acids arginine and glutamine are combined as the dipeptide arginyl-glutamine in order to provide beneficial effects in a safe, easily absorbable formulation. The dipeptide of the subject invention is particularly advantageous because the solubility of the dipeptide is greater than the individual amino acids.

Advantageously, the dipeptide of the subject invention inhibits the over-proliferation of unwanted blood vessels. The dipeptide of the subject invention is also advantageous because it is safe for human and animal use and can be readily formulated in an aqueous solution.

The compounds of the subject invention can be formulated according to known methods for preparing pharmaceutically useful compositions. Formulations are described in detail in a number of sources which are well known and readily available to those skilled in the art. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of the dipeptide compound or a salt or prodrug thereof, and one or more non-toxic, pharmaceutically acceptable carriers or diluents. Pharmaceutical carriers or excipients may contain inert ingredients which do not interact with the compound, or ingredients that do interact with the compound but not in a fashion so as to interfere with the desired effect. In general, the formulations are prepared by uniformly and intimately bringing into association the active ingredient with liquid carriers or finely divided solid carriers or both, and then, if necessary, shaping the product. Examples of such carriers for use in the invention include ethanol, dimethyl sulfoxide, glycerol, silica, alumina, starch, and equivalent carriers and diluents.

The dipeptide of the subject invention can also be formulated as a nutraceutical, including drinks, drink mixes, and bars.

DETAILED DISCLOSURE OF THE INVENTION

Figure 1:
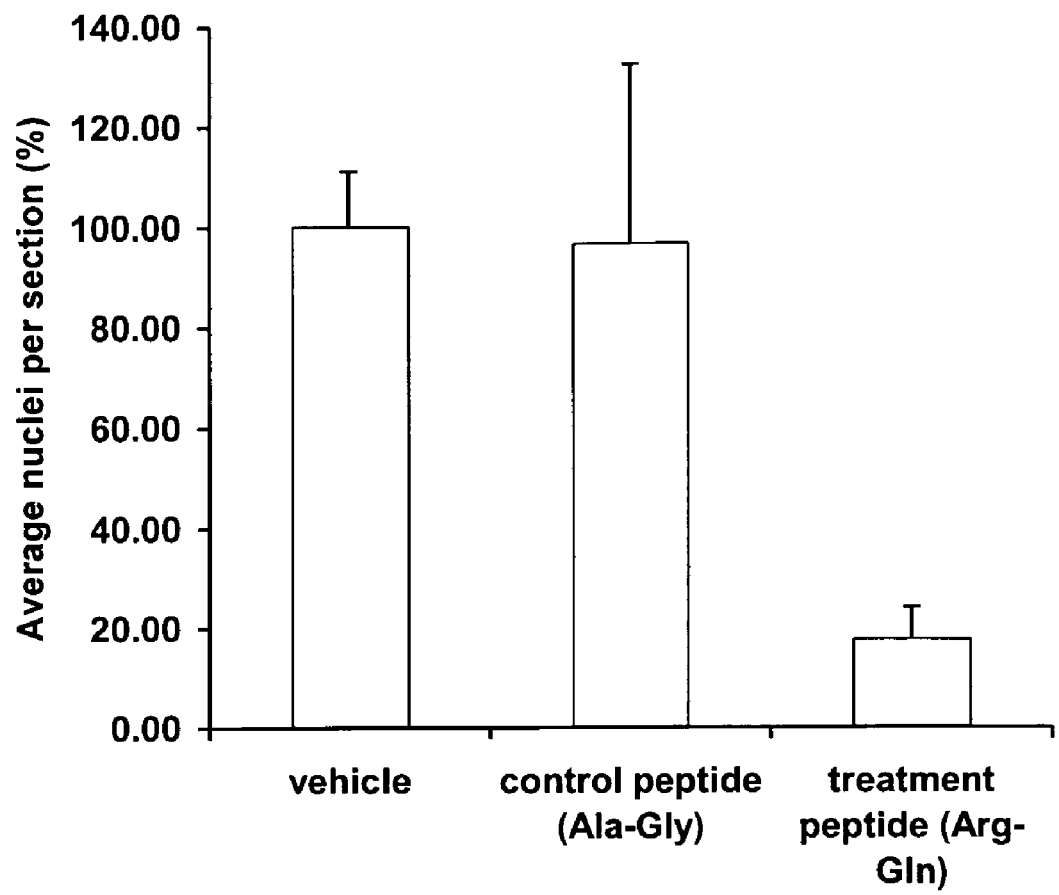
FIG. 1 shows inhibition of neovascularization by an arginyl-glutamine dipeptide in a model of retinopathy of prematurity.

The present invention provides compositions containing therapeutic dipeptides and methods for administering the same. In one embodiment, the subject invention provides a novel, safe and affordable therapy for treatment of pathological ocular vascular proliferation.

Advantageously, the subject invention provides a dipeptide having excellent water solubility, stability to sterilization, long-term stability, and bioavailability for humans and animals. One embodiment of the present invention provides a composition comprising an aqueous pharmaceutical solution having at least one arginyl-glutamine dipeptide. Other embodiments include nutraceutical formulations.

In a specific embodiment of the subject invention the arginyl-glutamine dipeptides described herein can be used for preventing the proliferation of abnormal retinal blood vessels in a patient. Thus, these dipeptides can be administered to premature infants or diabetics who are at risk for retinal disease.

In accordance with the teachings provided herein, aqueous clinical compositions can be prepared that include at least one arginyl-glutamine dipeptide. The dipeptide can be added to enteral or parenteral formulations. Each dipeptide has an N-terminal amino acid which is arginine. The C-terminal amino acid is glutamine.

The concentration of the dipeptide in the aqueous solution can be, for example, from about 0.1 to about 25.0 percent by weight. As discussed in more detail below, in addition to the dipeptides of the subject invention, the clinical solution can contain, for example, dextrose, liquid emulsions, vitamins, minerals, trace elements, and other components. The selection of the particular dipeptide formulation depends upon the particular use.

For parenteral administration, a supply of the dipeptide solution may be merged through a Y-connection with a supply of glucose solution or other parenteral solutions. The dipeptide solutions may also be mixed with glucose solutions and/or other parenteral solutions to create a mixture which may be administered parenterally.

The administration of dipeptides rather than free amino acids allows administration of the same amount of amino acid residue in solutions which are less hypertonic and therefore can be introduced into peripheral veins.

The dipeptides of the subject invention can be readily synthesized and/or formulated by a person skilled in the art having the benefit of the instant disclosure. Alternatively, the dipeptides can be purchased commercially from, for example, Bachem Biosciences, Inc. which sells the H-Arg-Gln-OH salt.

The subject invention contemplates the administration of the Arg-Gln dipeptide in any appropriate formulation including, for example, salts, prodrugs (precursor), and extended release formulations (such as, for example, formulation with polyethylene glycol (PEG)). The peptide itself may be administered, as well as oligopeptides, peptides, proteins, protein hydrolysates, and any other materials that could serve as a source of the dipeptide.

In the case of oligopeptides, peptides, and proteins, these prodrug formulations may be designed with, for example, cleavage sites adjacent to each side of the dipeptide so that the dipeptide is generated upon exposure to enzymes, acids or other factors. In one embodiment, a polypeptide can be prepared with multiple dipeptides separated by linkers and/or cleavage sites, thereby creating multiple dipeptides upon exposure to the cleaving factor. This cleaving to create the dipeptide can be done as part of a production process or in vivo as the result of, for example, digestive enzymes and/or acids. The source of the dipeptide may be natural or the dipeptide (including prodrugs) may be produced recombinantly or synthetically.

In one embodiment, the dipeptide can be conjugated to a targeting moiety that directs the peptides to a desired location. The targeting moiety may be, for example, an antibody, receptor, and/or ligand.

In one method, the subject invention involves identifying an individual who has, or who is at risk for developing pathological vascularization and then providing that individual with a composition comprising the dipeptide of the subject invention (or a prodrug thereof) along with instructions or information concerning the activity of the dipeptide to inhibit pathological vascularization. In one embodiment, a nutriceutical is provided that has the dipeptide, and/or a salt or prodrug thereof, along with instructions for consuming the nutriceutical to promote cardiovascular (or just vascular) health.

The compounds of the invention are useful for various therapeutic purposes. Specifically, as described herein, the compounds of the invention are effective for inhibiting vascular retinopathy and other forms of pathological vascular proliferation. Accordingly, these compounds are useful prophylactically and therapeutically for treating animals, including humans and other mammals, at risk for pathological vascular proliferation including vascular retinopathy and vasculature associated with tumors.

Therapeutic application of the compounds and compositions containing them can be accomplished by any suitable therapeutic method and technique presently or prospectively known to those skilled in the art.

The peptides provided by the present invention are typically administered to a mammal, particularly a human, dog or cat, any of which is intended to be encompassed by the term "patient" herein, in need of the prevention or treatment of pathological vascular proliferation. Pathological conditions involving vascular proliferation include, for example, tumor growth, age-related macular degeneration, vascular proliferation associated with angioplasty and/or stents, diabetic retinopathy and retinopathy of prematurity. Thus, the dipeptides of the subject invention can be used to treat angiogenic diseases. Angiogenic diseases include those that are disclosed in U.S. Pat. No. 5,759,547, which is incorporated herein, in its entirety, by reference.

Angiogenesis and neovascularization in the adult animal is usually a pathological process, and is in direct contradistinction to non-pathological neovascularization, which usually occurs in normal embryogenesis (e.g., development of the embryonic vascular system). In accordance with the subject invention, neovascularization refers specifically to pathological neovascularization. Aberrant or pathological vascularization is a key component in numerous disease states. For example, vascularization is a critical element of most solid tumors, such as cancers of the brain, genitourinary tract, lymphatic system, stomach, larynx and lung. These include histiocytic lymphoma, lung adenocarcinoma and small cell lung cancers. Aberrant vascular growth in the retina can lead to visual degeneration which can culminate in blindness. Accordingly, the subject invention provides dipeptide compounds and formulations thereof for the treatment of neovascularization.

Compounds of the invention can also be used to inhibit the proliferation of vascular endothelial cells and so are indicated for use in treating graft vessel diseases such as restenosis or vascular occlusion following vascular insult such as angioplasty, allo- or xenotransplant vasculopathies, graft vessel atherosclerosis, and in the transplantation of an organ (e.g., heart, liver, lung, kidney or pancreatic transplants (Weckbecker et al., *Transplantation Proceedings* 1997, 29, 2599–2600).

The peptides are administered by incorporating the peptide in a pharmaceutical composition comprising the peptide or a non-toxic pharmaceutically acceptable salt or prodrug thereof and a non-toxic pharmaceutically acceptable carrier therefor.

The peptide, or its salt or prodrug, is employed in an effective amount i.e. an amount sufficient to evoke the desired pharmacological response. This is generally an amount sufficient to produce lessening of one or more of the effects of pathological vascular proliferation. In the case of retinopathy, it is an amount sufficient to produce regression of neovascularization and/or an amount sufficient to produce improved visual acuity.

The terms "pharmaceutically acceptable carrier" or a "carrier" refer to any generally acceptable excipient or drug delivery device that is relatively inert and non-toxic. The peptide can be administered with or without a carrier. When treating retinopathies, a preferred embodiment is to administer the peptide to the retinal area or the vasculature around or leading to the retina. Exemplary carriers include calcium carbonate, sucrose, dextrose, mannose, albumin, starch, cellulose, silica gel, polyethylene glycol (PEG), dried skim milk, rice flour, magnesium stearate, and the like. The peptide can be administered systemically or locally (e.g., by injection or diffusion). Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer the peptide.

Suitable non-toxic pharmaceutically acceptable carriers for use with the peptide will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985). The choice of suitable carriers will depend upon the exact nature of the particular dosage form selected.

The supplement can take on various forms, including but not limited to pills, edible bars, drinks or drink mix. The compounds of the subject invention may be combined with other components such as, for example, a soluble fiber compound. The soluble fiber compound may be, for example, locust gum, guar gum, pectin, gum arabic, or psyllium.

The person skilled in this art, having the benefit of the current disclosure can readily formulate the compounds of the subject invention into a pill, bar, or other edible composition for easy and enjoyable consumption. These therapeutic compositions can be used as described herein.

In one embodiment, the present invention provides a nutriceutical compositions. The dipeptides can be obtained or produced using processes known to those skilled in the art having the benefit of the instant disclosure.

The compositions of the invention are useful for various therapeutic purposes. Because of the antiproliferative properties of the compounds, they are useful to prevent unwanted cell growth in a wide variety of settings including in vitro uses.

Therapeutic application of the new compositions can be accomplished by any suitable therapeutic method and technique presently or prospectively known to those skilled in the art.

When used to reduce the severity or incidence of tumors, the dosage administration to a host in the above indications will be dependent upon the identity of the cancer cells, the type of host involved, its age, weight, health, kind of concurrent treatment, if any, frequency of treatment, and therapeutic ratio.

In a preferred embodiment, the active ingredient at the site of treatment is the dipeptide of the subject invention in the absence of other amino acids. Thus, it is not necessary for the subject invention to be specifically formulated with, for example, an essential amino acid and a non-essential amino acid.

In one embodiment, the dipeptide of the subject invention can be administered as a nutriceutical supplement in unit dosage form. In such form, the preparation is subdivided into unit doses containing appropriate quantities of the nutriceutically active component. The unit dosage form can be a packaged preparation, such as packeted tablets, capsules, lotions, ointments and powders in vials or ampoules. Also, the unit dosage can be a drink (such as a powder-based drink, shake or tea formulation), yogurt, solid food product, capsule, tablet, lotion, ointment, chewing gum, lozenge, or it can be the appropriate number of any of these in packaged form.

In one embodiment, there is provided a nutriceutical of the present invention in the form of a food bar. The food bar, which may be cooked or non-cooked, may contain a grain or grains, nuts, possibly dried fruit, sweeteners and other ingredients that may be mixed with a binder, such as a sugar syrup or shortening, and formed into "bars" of desirable size. Generally, food bars are prepared in bar form of a manageable size for a product of this nature, and bearing in mind both package size and time required for consumption, weigh in the range of 2–3 ounces.

The food bar of the present invention may contain an amount of protein in addition to significant amounts of complex and simple carbohydrate, such as those non-cooked food bars described by U.S. Pat. No. 4,055,669. Further, the food bar of the present invention may contain dietary fiber to aid in the normalization of bowel function and reduce the risk of colonic diseases. There are presently available a number of non-cooked food bars that provide varying amounts of dietary fiber while possessing requisite qualities of acceptable taste and texture, including food bars described in U.S. Pat. Nos. 4,673,578 and 4,871,557.

The therapeutic dosage range can be determined by one skilled in the art having the benefit of the current disclosure. Naturally, such therapeutic dosage ranges will vary with the size, species and physical condition of the patient, the severity of the patient's medical condition, the particular dosage form employed, the route of administration and the like. In addition, a route of administration may be selected to slowly release the chemical, e.g., slow intravenous infusion.

One embodiment of the current invention envisions parenteral administration, especially intravenous administration, as the route of administration. Parenteral dosage forms should be sterile and pyrogen-free, and are prepared in accord with accepted pharmaceutical procedures. The parenteral formulations may be organic or aqueous or mixed organic/aqueous formulations and may further contain antioxidants, buffers, bacteriostats, isotonicity adjusters and like additions acceptable for parenteral formulations. In a preferred embodiment, the parenteral formulation contains an effective amount of the peptide of the subject invention in an aqueous solution.

For parenteral application, particularly suitable are injectable, sterile solutions, preferably oily or aqueous solutions, as well as suspensions, emulsions, or implants. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

Also, according to the subject invention, the local administration of the dipeptide compounds, and formulations thereof, by means of a drug delivery device or implant placed in proximity to the local tissue site provides for the maintenance of efficacious, safe levels of active drug ingredient at the local tissue disease site.

According to the subject invention, the local ocular administration of dipeptide compounds of the invention, and/or formulations thereof, attenuate ocular pathological disease processes. Thus, local ocular administration of a dipeptide compound of the invention, and/or formulations thereof, provides for an efficacious but safe controlled concentration range of the dipeptide directly in the eye.

Ocular dipeptide-based therapies, as describe herein, provide significant advantages for treating neovascular ocular disease relative to current laser surgery treatment modalities including panretinal photocoagulation, which can be accompanied by extensive ocular tissue damage. In the examples of posterior neovascular ocular diseases, such as age related macular degeneration and diabetic retinopathy, target ocular pathologies and tissues for treatment are especially localized to the retinal, choroidal and corneal ocular compartments.

Preferably, the peptide is administered locally to the eye, retinal area, choroid area or associated vasculature. The peptide can also be administered to the cornea of the eye.

The peptide diffuses into the eye and contacts the retina or surrounding vasculature (e.g., eye drops, creams or gels).

The dipeptide compounds of the present invention, and formulations thereof, are advantageous because they overcome problems associated with stability, toxicity, lack of target tissue specificity, safety, efficacy, extent and variability of bioavailability.

As contemplated in the subject invention, where a dipeptide compound is in the form of a prodrug, the prodrug can be converted to a biologically active compound at a controlled rate via passive (such as by aqueous hydrolysis) or biologically mediated (such as biocatalytic or enzymatic) mechanisms. An advantage of the in vivo conversion of the prodrug is that the ensuing dipeptide provides localized therapeutic effects in target disease tissue with high therapeutic margins of safety.

A further embodiment provides the use of dipeptide compounds in conjunction with a drug delivery system in the form of an implant or a device for the treatment of conditions as set forth herein. Certain embodiments of the invention contemplate the use of dipeptide compounds and formulations thereof for use as coatings for example in conjunction with physical implants such as stents and band ligatures. Therapeutic uses of such implants include but are not limited to vascular diseases such as restenosis, and in bone and tissue grafts.

A further embodiment of the subject invention provides for the local administration of dipeptide compounds in combination with other pharmacological therapies. As contemplated in the subject invention, combination therapies of dipeptide compounds with other medicaments targeting similar or distinct disease mechanisms have advantages of greater efficacy and safety relative to respective monotherapies with either specific medicament.

In one embodiment, a dipeptide compound is used to treat neovascular ocular disease by localized (for example, in ocular tissue) concurrent administration with other medicaments that act to block angiogenesis by pharmacological mechanisms. Medicaments that can be concurrently administered with a dipeptide compound of the invention include, but are not limited to, vascular endothelial growth factor VEGF blockers (e.g. by VEGF neutralizing binding molecules such as MACUGEN® (Eyetech) and LUCENTIS® (ranibizumab, Genentech), Squalamine lactate (Genaera Corporation); and VEGF tyrosine kinase inhibition) for treating neovascular ocular disease (AMD and Diabetic Retinopathy) and glucocorticoids (e.g. Triamcinolone) for treating macular edema.

One or more active agents can be administered. When administering more than one, the administration of the agents can occur simultaneously or sequentially in time. The agents can be administered before and after one another, or at the same time. The methods also include co-administration with other drugs that are used to treat retinopathy or other diseases described herein.

The composition can be administered in a single dose or in more than one dose over a period of time to confer the desired effect.

The dosage administration to a host in the above indications will be dependent upon the specific condition being treated, the type of host involved, its age, weight, health, kind of concurrent treatment, if any, frequency of treatment, and therapeutic ratio. Those skilled in the art will be able to determine the appropriate dosages depending on these and other factors. Typically, a therapeutically effective amount of the compound can range from about 1 mg per day to about 1000 mg per day for an adult human animal. For oral administration to human adults, a dosage of 0.01 to 100 mg/kg/day, preferably 0.01–1 mg/kg/day, is generally a therapeutically effective amount.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent.

In a retinal cell culture model used to study the effects of the dipeptide on transepithelial resistance (TER) and vascular endothelial growth factor (VEGF), it was demonstrated that the dipeptide increased TER and decreased VEGF, both desirable effects that have been associated with a decrease in vascular proliferative retinal disease.

All patents, patent applications, provisional applications, and publications referred to or cited herein are incorporated by reference in their entirety to the extent they are not inconsistent with the explicit teachings of this specification.

Following is an example which illustrates procedures for practicing the invention. This example should not be construed as limiting. All percentages are by weight and all solvent mixture proportions are by volume unless otherwise noted.

EXAMPLE 1

Use of Arginyl-glutamine to Prevent Retinopathy of Prematurity

Neonatal mice were exposed to a period of hyperoxia to induce retinal angiogenesis that mimics retinopathy of prematurity. An Arginyl-glutamine dipeptide was administered intraperitoneally twice daily during the period when neovascularization occurs in this model, days 12 through 17.

On day 17 the animals are sacrificed and degree of angiogenesis was quantified by counting pre-retinal neovascularization on stained sections from treated and untreated animals.

The data summarized in FIG. 1 represent combined data from two separate experiments. The results demonstrated a statistically significant effect of the dipeptide (argininyl-glutamine) compared to vehicle and dipeptide (alaninyl-glycine). Treatment of the pups with the dipeptide (arginiyl-glutamine) resulted in a 80% reduction in preretinal neovascularization.

Figure 2:
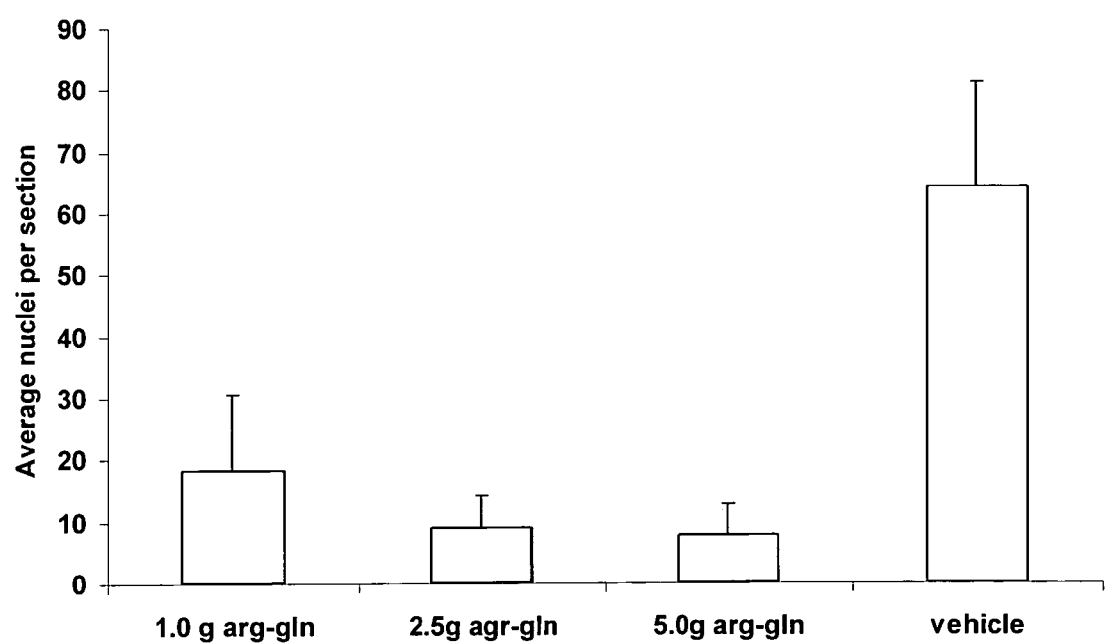
FIG. 2 shows inhibition of neovascularization by an arginyl-glutamine dipeptide in a model of retinopathy of prematurity at various concentrations of the dipeptide.

This experiment has been repeated with different doses of the dipeptide compared to the vehicle. The results are shown in FIG. 2. This shows a clear decrease in nuclei (associated with decreased retinopathy) in the animals receiving the dipeptide after the oxygen stress challenge that is known to induce retinopathy.

EXAMPLE 2

Nutritional Composition for Enteral Administration

The inventive composition that contains the subject dipeptide may be a nutritional composition (nutritionally complete or nutritional supplement) for enteral administration. That is, it is designed for oral, intragastric, or transpyloric use. The composition of the invention may be an infant formula or adult nutritional composition that can be milk-based, soy-based, or based on other food sources. The composition may be prepared as a powder or liquid nutritional composition for formulas prepared for infant, pediatric and adult populations. The inventive composition may be prepared as a nutritionally complete diet by including vitamins and minerals at acceptable levels. The subject composition can be in the form of a dietary product such as an infant formula, milk substitute, and meal replacement or supplement.

One embodiment of the invention is a dietary supplement that contains arginyl-glutamine dipeptide, or a precursor thereof. The dietary supplement is designed to be administered along with a food or nutritional composition, such as infant formula, and can either be intermixed with the food or nutritional composition prior to ingestion by the subject, or can be administered to the subject either before or after ingestion of a food or nutritional composition. The subject dietary supplement contains an amount of arginyl-glutamine dipeptide, or a precursor thereof, that is effective for the prevention or treatment of retionoathy of prematurity, diabetic retinopathy, vascular proliferative retinopathy, or proliferation of abnormal vascularization, and the like.

In one embodiment, a novel infant formula containing arginyl-glutamine dipeptide, or precursor thereof, is nutritionally complete. By the term "nutritionally complete" is meant that the composition contains adequate nutrients to sustain healthy human life for extended periods. The infant formula of the invention contains ingredients which are designed to meet the nutritional needs of the human infant namely, a protein, carbohydrate and lipid source and other nutrients such as vitamins and minerals.

Besides the subject dipeptide, the composition of the invention contains a nitrogen source (i.e., amino acids and/or protein) in an amount that is typically about 1 g to about 10 g per 100 kcal of total composition, preferably about 2 g to about 6 g per 100 kcal; the amount of lipid source per 100 kcal of total composition is typically greater than 0 g up to about 6 g, preferably about 0.5 g to about 5.5 g and more preferably about 2 g to about 5.5 g; and the amount of non-fiber carbohydrate source per 100 kcal of total composition is typically about 5 g to about 20 g, preferably about 7.5 g to about 15 g. The amount of vitamins and minerals in the nutritionally complete composition is typically sufficient to meet 100% of the U.S. recommended daily intake (RDI) in about 500 to about 3,000 kcal, preferable is about 1,000 to about 3,000 kcal.

In one embodiment of the present nutritional composition the amount of vitamins and minerals is sufficient to meet 100% of the RDI in about 500 to about 3,000 kcal, preferably in about 1,000 to about 3,000 kcal. As used herein, the RDI's are intended to mean those published in the Federal Register, Vol. 58, No. 3, Wednesday, Jan. 6, 1993, page 2227 which are as follows: Vitamin A, 5,000 International Units; Vitamin C, 60 milligrams; Thiamin, 1.5 milligrams; Riboflavin, 1.7 milligrams; Niacin, 20 milligrams; Calcium, 1.0 gram; Iron, 18 milligrams; Vitamin D, 400 International Units; Vitamin E, 30 International Units; Vitamin $B_6$, 2.0 milligrams; Folic acid, 0.4 milligrams; Vitamin $B_{12}$, 6 micrograms; Phosphorus, 1.0 gram; Iodine, 150 micrograms; Magnesium, 400 milligrams; Zinc, 15 milligrams; Copper, 2 milligrams; Biotin, 0.3 milligram; Pantothenic acid, 10 milligrams.

In one embodiment, the novel infant formula contains the arginyl-glutamine dipeptide, or a precursor thereof, in an amount that is less than 0.1% by weight of the formula. It is preferred that the amount of arginyl-glutamine dipeptide in the formula is from about 0.001% to 0.098% by weight of the formula, more preferred is an amount of from about 0.01% to 0.098% by weight.

In the present method, the subject infant formula or dietary supplement is administered to an infant in an amount that is sufficient to prevent or treat retinopathy of prematurity, diabetic retinopathy, vascular proliferative retinopathy, or proliferation of abnormal vascularization. In a preferred embodiment, that amount is from about 0.001 to about 10,000 mg/kg of body weight of the subject per day, more preferred is an amount of from about 0.01 to about 1000 mg/kg/day, yet more preferred is about 0.01 to about 50 mg/kg/day, and even more preferred is about 0.1 to about 10 mg/kg/day. Alternatively, the amount administered to an infant is from about 1 mg to about 10,000 mg/day, preferably abut 10 mg to about 1000 mg, and yet more preferred about 10 mg to about 500 mg.

The protein source that is present in addition to the subject dipeptide can be non-fat milk solids, a combination of non-fat milk solids and whey protein, a partial hydrolysate of non-fat milk and/or whey solids, soy protein isolates, or partially hydrolyzed soy protein isolates. The infant formula can be casein predominant or whey predominant.

The carbohydrate source in the infant formula can be any suitable carbohydrate known in the art to be suitable for use in infant formulas. Typical carbohydrate sources include sucrose, fructose, glucose, maltodextrin, lactose, corn syrup, corn syrup solids, rice syrup solids, rice starch, modified corn starch, modified tapioca starch, rice flour, soy flour, and the like.

The lipid source in the infant formula can be any lipid or fat known in the art to be suitable for use in infant formulas. Typical lipid sources include milk fat, safflower oil, egg yolk lipid, olive oil, coconut oil, palm oil, palm kernel oil, soybean oil, sunflower oil, fish oil and fractions derived thereof such as palm olein, medium chain triglycerides (MCT), and esters of fatty acids wherein the fatty acids are, for example, arachidonic acid, linoleic acid, palmitic acid, stearic acid, docosahexaenoic acid, eicosapentaenoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil. Medium chain triglycerides contain higher concentrations of caprylic and capric acid than typically found in conventional oils, e.g., approximately three-fourths of the total fatty acid content is caprylic acid and one-fourth is capric acid.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to compensate for some loss during processing and storage of such compositions.

To select a specific vitamin or mineral compound to be used in the infant formula of the invention requires consideration of that compound's chemical nature regarding compatibility with the particular processing conditions used and shelf storage.

Examples of minerals, vitamins and other nutrients optionally present in the composition of the invention include vitamin A, vitamin $B_6$, vitamin $B_{12}$, vitamin E, vitamin K, vitamin C, folic acid, thiamine, inositol, riboflavin, niacin, biotin, pantothenic acid, choline, calcium, phosphorus, iodine, iron, magnesium, copper, zinc, manganese, chloride, potassium, sodium, selenium, chromium, molybdenum, taurine, and L-carnitine. Minerals are usually added in salt form. In addition to compatibility and stability considerations, the presence and amounts of specific minerals and other vitamins will vary somewhat depending on the intended infant population.

The infant formula of the invention also typically contains emulsifiers and stabilizers such as soy lecithin, carrageenan, and the like.

The infant formula of the invention may optionally contain other substances which may have a beneficial effect such as lactoferrin, nucleotides, nucleosides, immunoglobulins, and the like.

The infant formula of the invention is in concentrate liquid form, liquid ready to consume form, or powder form. Of course, if in powder form, the formula is diluted to normal strength with water to be in a form ready to consume.

The osmolality of the liquid infant formula of the invention (when ready to consume) is typically about 100 to 1100 mOsm/kg $H_2O$, more typically about 200 to 700 mOsm/kg $H_2O$.

The infant formula of the invention can be sterilized, if desired, by techniques known in the art, for example, heat treatment such as autoclaving or retorting, and the like.

The infant formula of the invention can be packaged in any type of container known in the art to be used for storing nutritional products such as glass, lined paperboard, plastic, coated metal cans and the like.

The infant formula of the invention is shelf stable after reconstitution. By "shelf stable" is meant that the formula in a form ready to consume remains in a single homogenous phase (i.e., does not separate into more than one phase upon visual inspection) or that the thickener does not settle out as a sediment upon visual inspection after storage overnight in the refrigerator. With the thickened nature of the product, the formula of the invention also has the advantage of remaining fluid (i.e., does not gel into a solid mass when stored overnight in the refrigerator).

In the method of the invention, infant formula comprising arginyl-glutamine dipeptide, or a precursor thereof, is administered to an infant. The form of administration is oral, which includes tube feeding.

The invention provides a commercially acceptable product in terms of desired stability and physical characteristics and the product demonstrates little to no observable browning effect by-products associated with a Maillard reaction. Further, the inventive composition is substantially homogeneous for an acceptable period after reconstitution (or for the shelf-life if prepared as a liquid). The invention is particularly useful for infant formula preparations for the prevention and treatment of retinopathy of prematurity, although it is equally applicable to other elemental diets specific to a selected population that is at risk of, or is suspected of having, diabetic retinopathy, vascular proliferative retinopathy, or proliferation of abnormal vascularization, and the like.

It should be understood that the examples and embodiments described herein are for illustrative purposes only and that various modifications or changes in light thereof will be suggested to persons skilled in the art and are to be included within the spirit and purview of this application.

We claim:

1. A method for inhibiting pathological ocular vascular proliferation in a subject in need thereof wherein the method comprises administering an effective amount, to the site or ocular vascular proliferation, of the dipeptide arginyl-glutamine, or a salt thereof.

2. The method, according to claim 1, wherein the ocular vascular proliferation being inhibited is in a mammal.

3. The method, according to claim 1, wherein said dipeptide, or salt thereof is administered in an aqueous formulation.

* * * * *

UNITED STATES PATENT AND TRADEMARK OFFICE
CERTIFICATE OF CORRECTION

PATENT NO. : 7,148,199 B2 Page 1 of 1
APPLICATION NO. : 10/951150
DATED : December 12, 2006
INVENTOR(S) : Josef Neu and Maria Grant It is certified that error appears in the above-identified patent and that said Letters Patent is hereby corrected as shown below:

Column 14,
Lines 28-29, "site or ocular" should read --site of ocular --.

Signed and Sealed this

Twenty-fourth Day of April, 2007

JON W. DUDAS
*Director of the United States Patent and Trademark Office*